United States Patent [19]

Wu et al.

[11] Patent Number: 6,084,145
[45] Date of Patent: Jul. 4, 2000

[54] DEHYDROGENATION CATALYST AND DEHYDROGENATION PROCESS USING SAID CATALYST

[75] Inventors: An-Hsiang Wu, Bartlesville; Charles A. Drake, Nowata, both of Okla.

[73] Assignee: Phillips Petroleum Company, Bartlesville, Okla.

[21] Appl. No.: 09/056,238

[22] Filed: Apr. 7, 1998

[51] Int. Cl.[7] .................................................. C07C 5/333
[52] U.S. Cl. ............................................. 585/662; 502/64
[58] Field of Search ........................ 502/60, 64; 585/662

[56] References Cited

U.S. PATENT DOCUMENTS

| | | | |
|---|---|---|---|
| 2,419,997 | 5/1947 | Houdry | 585/602 |
| 3,216,789 | 11/1965 | Breck et al. | 23/113 |
| 3,236,910 | 2/1966 | Bukata et al. | 260/683.3 |
| 4,202,758 | 5/1980 | O'Hara et al. | 208/143 |
| 4,680,280 | 7/1987 | Pandey et al. | 502/66 |
| 5,292,697 | 3/1994 | Klotz | 502/73 |
| 5,898,011 | 4/1999 | Wu et al. | 502/60 |

*Primary Examiner*—Tom Dunn
*Attorney, Agent, or Firm*—Ryan N. Cross

[57] ABSTRACT

A dehydrogenation catalyst is produced by a process comprising the steps of: mixing an L-zeolite, chromium(VI) oxide, a binder, and an acid to form a mixture; and calcining the mixture at a temperature of about 200–800° C. A paraffin having 2–7 carbon atoms per molecule can be contacted with the above-described catalyst under dehydrogenation conditions to produce olefins having the same number of carbon atoms per molecule as the paraffin.

30 Claims, No Drawings

DEHYDROGENATION CATALYST AND DEHYDROGENATION PROCESS USING SAID CATALYST

BACKGROUND OF THE INVENTION

This invention relates to dehydrogenation of paraffins to olefins and catalysts for catalytically promoting such dehydrogenation.

It is known to prepare dehydrogenation catalysts from a zeolite and a metal promoter, such as a chromium(III) compound. Heretofore, however, dehydrogenation of a paraffin using such prior catalysts have produced a product gas having a disappointingly low weight percentage of the desired olefins.

SUMMARY OF THE INVENTION

It is, therefore, an object of the invention to provide a dehydrogenation catalyst for converting a paraffin to olefins in a process which produces a product gas having a desirably high weight percentage (i.e. substantially above 10) of olefins.

According to one aspect of the invention, there is provided a dehydrogenation catalyst produced by a process comprising the steps of: mixing an L-zeolite, chromium(VI) oxide ($CrO_3$), a binder, and an acid to form a mixture; and calcining the mixture at a temperature of about 200–800° C.

According to another aspect of the invention, there is provided a process for dehydrogenation of a paraffin having 2–7 carbon atoms per molecule, wherein the paraffin is contacted with the above-described catalyst under dehydrogenation conditions to produce olefins having the same number of carbon atoms per molecule as the paraffin.

A subsequent example demonstrates that a catalyst of the invention as used in the dehydrogenation of a paraffin produces a product gas having an unexpectedly high weight percentage (about 17 weight percent) of olefins after over 7 hours into the run. In addition to this highly desirable result, the catalyst of the invention proves to be highly selective (over 95%) in the conversion of the paraffin to olefins, and, where an n-paraffin is used, no undesirable isomeric olefins are produced.

DETAILED DESCRIPTION OF THE INVENTION

The components used in the above-mentioned mixing step will now be described in more detail. The weight percentage given for each component is based upon the total weight of the components.

L-zeolite is a type of synthetic zeolite which has been extensively described and characterized in patents and other literature. L-zeolite has a highly distinctive X-ray diffraction pattern, such as that disclosed in U.S. Pat. No. 3,216,789 of Breck et al. The crystal structure of L-zeolite is characterized by 12-membered rings defining channels and cages. A preferred composition of L-zeolite can be expressed in terms of mole fractions of oxides according to the following formula:

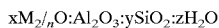

$xM_{2/n}O:Al_2O_3:ySiO_2:zH_2O$ wherein x is about 0.9–1.3, M designates at least one exchangeable cation, n is the valence of M, y is about 5.2–6.9, and z is about 0–9. M is most preferably potassium (where n=1) such that the cations present are substantially all potassium cations. This form of L-zeolite, hereafter referred to as potassium L-zeolite, is commercially available as a powder, and can, prior to its use in catalyst preparation, be calcined at a temperature of about 200–800°, preferably about 400–600° C., for a time of about 1–5 hours in static air and at atmospheric pressure. Such calcination, which is desirable but optional, drives off any combustible contaminants and water that may be present in the pores of the L-zeolite.

Instead of using the preferred potassium L-zeolite in the mixture, potassium L-zeolite can optionally be subjected to ion exchange treatment in an aqueous solution of an appropriate salt so as to replace at least some of the potassium cations with other cations, such as, for example, lanthanum cations. According to one particular procedure, potassium L-zeolite is mixed with an aqueous lanthanum nitrate solution, and then heated at a temperature of about 90° C. for about 10–20 hours. The resulting L-zeolite, containing both potassium cations and lanthanum cations, is then washed, dried, and calcined as discussed above.

The amount of L-zeolite used in the mixing step can be, by way of example, about 20–60 weight percent, and more narrowly about 30–50 weight percent.

Chromium(VI) oxide is commercially available as a powder. The amount of chromium(VI) oxide used in the mixing step can be, by way of example, about 5–25 weight percent, and more narrowly about 10–20 weight percent.

The binder is preferably a metal oxide such as silica, titania, zirconia, alumina, or mixtures thereof. Alumina is preferred, and is, of course, commercially available as a powder. The amount of binder used in the mixing step can be, by way of example, about 10–30 weight percent, and more narrowly about 15–25 weight percent.

The acid is preferably in solution with a solvent to form an acidic solution, preferably comprising about 5–25 weight percent acid and about 75–95 weight percent solvent. The acid can be an organic acid, such as acetic acid, or an inorganic acid, such as hydrochloric or nitric acid. The solvent can be an organic solvent or water, but water is preferred. The amount of acidic solution used in the mixing step can be, by way of example, about 20–40 weight percent, and more narrowly about 25–35 weight percent.

Mixing of the above-described components is preferably performed under normal atmospheric conditions and at room temperature (about 25° C.) for a sufficient time to form a mixture having the consistency of an extrudable dough. A small quantity of components can be mixed manually, whereas larger quantities can be mixed in a suitable mixing apparatus with agitators. To achieve the most uniform mixture, it is desirable to first mix the L-zeolite, chromium (VI) oxide, and binder, followed by addition of the acid and further mixing to produce the desired mixture.

The doughy mixture is preferably extruded to form an extrudate, which is allowed to dry at room temperature under normal atmospheric conditions for about 2–5 hours. The dried extrudate is then placed in a suitable furnace and calcined at a temperature of about 200–800° C., more preferably about 300–700° C., and most preferably about 400–600° C. Calcination is preferably carried out in static air at atmospheric pressure. Time of calcination is preferably about 10 minutes–20 hours, most preferably about 1–10 hours. The resulting catalyst extrudate is taken out of the furnace and then fragmented into a plurality of cylindrically shaped catalyst pellets.

Dehydrogenation using the catalyst pellets is preferably carried out in a fixed bed downflow reactor at atmospheric pressure. Catalyst pellets, typically mixed with a catalytically inert filler material (i.e. alumina), are positioned in the reactor to form a fixed catalyst bed. Any spaces in the reactor not occupied by the catalyst bed are filled with filler material. The reactor and the catalyst bed therein are heated by a suitable furnace, preferably an electric furnace having coils surrounding the reactor.

Typically, the catalyst bed temperature is gradually increased to the desired temperature while only carrier gas, such as hydrogen, argon, nitrogen, or helium, flows downwardly through the reactor. Catalyst bed temperature is preferably about 200–800° C., more preferably about 300–700° C., and most preferably about 400–600° C. After the catalyst bed temperature has stabilized, a flow of paraffin feed is established in admixture with the carrier gas so that the paraffin/carrier gas mixture flows through the heated catalyst bed. The molar ratio of carrier gas to paraffin is preferably about 0.5–5, most preferably about 1. The WHSV (Weight Hourly Space Velocity) for the paraffin (in units of grams of paraffin/grams of catalyst/hour) is preferably about 1–10, more preferably about 2–8, and most preferably about 3–7. Contact of the paraffin with the heated catalyst pellets results in dehydrogenation of the paraffin to olefins having the same number of carbon atoms as the paraffin.

Any paraffin can be used in the dehydrogenation process which has 2–7 carbon atoms per molecule. A paraffin having 3–5 carbon atoms per molecule is preferred.

The product gas produced by the reactor goes to suitable separation equipment which separates the various components of the product gas. Components of the product gas will include paraffin that failed to dehydrogenate (preferably recycled back to the reactor), small amounts of other paraffin by-products, and the desired olefins.

Obviously, many modifications and variations of the present invention are possible in light of the above teachings. For example, the catalyst need not be in the form of cylindrical pellets, but could be in a granular or other form. It is, therefore, to be understood that within the scope of the appended claims, the invention may be practiced otherwise than as specifically described.

Examples 1–3 are set forth below. Example 1 demonstrates the superiority of the inventive catalyst (produced with chromium(VI) oxide), in dehydrogenation of a paraffin, as compared to the comparative catalysts (produced with chromium(III) oxide, $Cr_2O_3$) of Examples 2 and 3. Procedures and equipment employed in each of the examples will now be described.

The L-zeolite used in catalyst preparation is a commercially available potassium L-zeolite powder (from CU Chemie Uetikom AG of Switzerland) which is calcined at 500° C. in static air at atmospheric pressure for 2 hours. X-ray fluorescence analysis of a sample revealed 9 weight percent potassium, 21.7 weight percent silicon, and 6.8 weight percent aluminum. Composition in terms of molar fractions of oxides was determined to be $0.92K_2O:Al_2O_3:6.15SiO_2$.

Catalyst was prepared in each example according to the following procedure. Potassium L-zeolite powder, chromium(VI or III) oxide powder (from Aldrich Chemicals of Milwaukee, Wis.), and "Catapal D" transition alumina binder powder (from Vista Chemical Co. of Houston, Tex.) are manually (with a spatula) mixed together for about 10–15 minutes in a bowl. An acetic acid solution, comprising 10 weight percent acetic acid and 90 weight percent water, is then added and mixing is continued for about 10–15 additional minutes until the mixture is of the consistency of an extrudable dough. All mixing is performed at room temperature and under normal atmospheric conditions. The doughy mixture is extruded to form 1/16 inch extrudate. The extrudate is allowed to dry at room temperature under normal atmospheric conditions for about 3–4 hours. The dried extrudate is then placed in a muffle furnace and calcined at 538° C. for 6 hours in static air at atmospheric pressure. The resulting catalyst extrudate is removed from the muffle furnace and, after allowing to cool, is fragmented into cylindrically shaped catalyst pellets having a diameter of 1/16 inch and a length of 3/16 inch.

Dehydrogenation runs employed a vertical downflow reactor, essentially comprising a stainless steel pipe having an upper inlet and a lower outlet. The reactor pipe has a length of 50 inches, a wall thickness of 3/16 inch, and an inside diameter of 3/4 inch. "Alundum-36" alpha alumina (from PQ Corporation of Valley Forge, Pa.) is used as a filler material. The bottom 20 inches of the reactor pipe is filled with alumina, the middle 10 inches is filled with a mixture of catalyst pellets (5 mL) and alumina (5 mL) to form a fixed catalyst bed, and the top 20 inches is filled with alumina. The reactor pipe is surrounded by the coils of an electric heater.

A flow of only hydrogen carrier gas is established through the reactor, which is at atmospheric pressure, and the reactor is heated so as to gradually increase the temperature of the catalyst bed to about 550° C. After about 10–15 minutes this desired temperature can be stabilized. In beginning a dehydrogenation run, paraffin feed (n-butane) is then allowed to flow into and through the reactor in admixture with the hydrogen. The product gas produced in the reactor flows from the reactor outlet, through tubing to a sample injector (normally with its valve open to allow flow therethrough), and from the sample injector through some more tubing to a cold trap which removes heavies ($C_5$ and heavier paraffins). The remaining product gas goes to flare. At any time during the run, the sample injector can be activated to draw a small (5 microliter) sample from the product gas stream for analysis.

A sample of the product gas is analyzed by a GC-FID spectrometer (HP 5890 II) having a capillary DB-1 (60 m) column. Weight percentages of components of the product gas are obtained from spectra recorded by the spectrometer.

EXAMPLE 1 (INVENTION)

10 grams of potassium L-zeolite powder, 4 grams of chromium(VI) oxide powder, 6 grams of alumina binder powder, and 8 grams of acetic acid solution were used in the preparation of 15.78 grams of catalyst extrudate. 2.89 grams (5 mL) of catalyst pellets as produced from the catalyst extrudate were used in a dehydrogenation run characterized by the following parameters: n-butane flow rate of 6.00 L/hr.; WHSV for the n-butane of 4.929 grams of n-butane/grams of catalyst/hour; hydrogen flow rate of 6.00 L/hr.; and a molar ratio of hydrogen to n-butane of 1.115. A sample of the product gas was taken 7.40 hours into the run.

Analysis of the sample revealed the following: 0.306 weight percent $C_1$–$C_3$ paraffins; 0.000 weight percent isobutane; 81.930 weight percent n-butane; 7.056 weight percent trans-2-butene; 5.091 weight percent 1-butene; 0.000 weight percent isobutene; 5.202 weight percent cis-2-butene; and 0.415 weight percent $C_5$ and heavier paraffins.

With regard to conversion of n-butane to other hydrocarbons (including other paraffins and butenes), the above analysis data indicates 18.070 weight percent of such hydrocarbons. With regard to conversion of n-butane to butenes, the analysis data indicates 17.349 weight percent butenes, a desirably and unexpectedly high weight percentage. Accordingly, selectivity to butenes (17.349/18.070) was 96%. Moreover, the analysis data indicates that no detectable isobutene was produced.

EXAMPLE 2 (COMPARATIVE)

10 grams of potassium L-zeolite powder, 4 grams of chromium(III) oxide powder, 4 grams of alumina binder powder, and 8 grams of acetic acid solution were used in the preparation of 14.68 grams of catalyst extrudate. 2.49 grams (5 mL) of catalyst pellets as produced from the catalyst extrudate were used in a dehydrogenation run characterized by the following parameters: n-butane flow rate of 6.00 L/hr.; WHSV for the n-butane of 5.720 grams of n-butane/grams of catalyst/hour; hydrogen flow rate of 6.00 L/hr.; and a molar ratio of hydrogen to n-butane of 1.115. A sample of the product gas was taken 7.04 hours into the run.

Analysis of the sample revealed the following: 0.065 weight percent $C_1$–$C_3$ paraffins; 0.000 weight percent isobutane; 92.879 weight percent n-butane; 2.586 weight percent trans-2-butene; 1.940 weight percent 1-butene; 0.000 weight percent isobutene; 1.930 weight percent cis-2-butene; and 0.600 weight percent $C_5$ and heavier paraffins.

With regard to conversion of n-butane to other hydrocarbons (including other paraffins and butenes), the above analysis data indicates 7.121 weight percent of such hydrocarbons. With regard to conversion of n-butane to butenes, the analysis data indicates 6.456 weight percent butenes. This weight percentage is considerably less than the weight percentage of butenes (17.349) obtained in Example 1 in accordance with the invention. Selectivity to butenes (6.456/7.121) was 90.7%, considerably less than the 96% obtained in Example 1. Like Example 1, the analysis data indicates that no detectable isobutene was produced.

EXAMPLE 3 (COMPARATIVE)

5 grams of potassium L-zeolite powder, 1.4 grams of chromium(III) oxide powder, 3 grams of alumina binder powder, and acetic acid solution (number of grams not recorded) were used in the preparation of 7.44 grams of catalyst extrudate. 2.54 grams (5 mL) of catalyst pellets as produced from the catalyst extrudate were used in a dehydrogenation run characterized by the following parameters: n-butane flow rate of 5.70 L/hr.; WHSV for the n-butane of 5.327 grams of n-butane/grams of catalyst/hour; hydrogen flow rate of 6.30 L/hr.; and a molar ratio of hydrogen to n-butane of 1.232. A sample of the product gas was taken 7.54 hours into the run.

Analysis of the sample revealed the following: 0.257 weight percent $C_1$–$C_3$ paraffins; 0.142 weight percent isobutane; 90.694 weight percent n-butane; 3.409 weight percent trans-2-butene; 2.739 weight percent 1-butene; 0.000 weight percent isobutene; 2.577 weight percent cis-2-butene; and 0.182 weight percent $C_5$ and heavier paraffins.

With regard to conversion of n-butane to other hydrocarbons (including other paraffins and butenes), the above analysis data indicates 9.306 weight percent of such hydrocarbons. With regard to conversion of n-butane to butenes, the analysis data indicates 8.725 weight percent butenes. This weight percentage is considerably less than the weight percentage of butenes (17.349) obtained in Example 1 in accordance with the invention. Selectivity to butenes (8.725/9.306) was 93.8%, less than the 96% obtained in Example 1. Like Example 1, the analysis data indicates that no detectable isobutene was produced.

What is claimed is:

1. A dehydrogenation catalyst produced by a process comprising the steps of:

mixing an L-zeolite, chromium(VI) oxide, a binder, and an acid to form a mixture; and calcining the mixture at a temperature of about 200–800° C.

2. A dehydrogenation catalyst as recited in claim 1 wherein the L-zeolite is potassium L-zeolite.

3. A dehydrogenation catalyst as recited in claim 2 wherein the amount of L-zeolite used in the mixing step is about 20–60 weight percent.

4. A dehydrogenation catalyst as recited in claim 3 wherein the amount of chromium(VI) oxide used in the mixing step is about 5–25 weight percent.

5. A dehydrogenation catalyst as recited in claim 1 wherein the binder is a metal oxide.

6. A dehydrogenation catalyst as recited in claim 5 wherein the metal oxide is alumina.

7. A dehydrogenation catalyst as recited in claim 6 wherein the amount of binder used in the mixing step is about 10–30 weight percent.

8. A dehydrogenation catalyst as recited in claim 1 wherein the acid is in solution with a solvent to form an acidic solution.

9. A dehydrogenation catalyst as recited in claim 8 wherein the acidic solution comprises about 5–25 weight percent acid and about 75–95 weight percent solvent.

10. A dehydrogenation catalyst as recited in claim 9 wherein the acid is acetic acid.

11. A dehydrogenation catalyst as recited in claim 10 wherein the solvent is water.

12. A dehydrogenation catalyst as recited in claim 11 wherein the amount of acidic solution used in the mixing step is about 20–40 weight percent.

13. A dehydrogenation catalyst as recited in claim 1 wherein the catalyst production process further comprises extruding the mixture to form an extrudate which is then calcined.

14. A dehydrogenation catalyst as recited in claim 1 wherein calcining is carried out at a temperature of about 300–700° C.

15. A dehydrogenation catalyst as recited in claim 14 wherein calcining is carried out at a temperature of about 400–600° C.

16. A dehydrogenation catalyst as recited in claim 15 wherein calcining is carried out for a time of about 10 minutes–20 hours.

17. A dehydrogenation catalyst as recited in claim 16 wherein calcining is carried out for a time of about 1–10 hours.

18. A process for dehydrogenation of a paraffin having 2–7 carbon atoms per molecule comprising: contacting the paraffin under dehydrogenation conditions with a catalyst produced by a process comprising (i) mixing an L-zeolite, chromium(VI) oxide, a binder, and an acid to form a mixture, and (ii) calcining the mixture at a temperature of about 200–800° C., whereby olefins are produced having the same number of carbon atoms per molecule as the paraffin.

19. A process as recited in claim 18 wherein the paraffin has 3–5 carbon atoms per molecule.

20. A process as recited in claim 19 wherein the paraffin is n-butane and wherein olefins produced by the process are butenes.

21. A process as recited in claim 18 wherein dehydrogenation conditions include a catalyst temperature of about 200–800° C.

22. A process as recited in claim 21 wherein the catalyst temperature is about 300–700° C.

23. A process as recited in claim 22 wherein the catalyst temperature is about 400–600° C.

24. A process as recited in claim 18 wherein the catalyst is in the form of a fixed catalyst bed, and wherein the paraffin is contacted with the catalyst by maintaining a flow of the paraffin in admixture with a carrier gas through the fixed catalyst bed.

25. A process as recited in claim 24 wherein the molar ratio of carrier gas to paraffin is about 0.5–5.

26. A process as recited in claim 25 wherein the WHSV for the paraffin is about 1–10 grams of paraffin/grams of catalyst/hour.

27. A process as recited in claim 18 wherein the L-zeolite is potassium zeolite, the binder is alumina, and the acid is acetic acid in solution with water to form an acidic solution comprising about 5–25 weight percent acetic acid and about 75–95 weight percent water.

28. A process as recited in claim 27 wherein the amounts of components used in the mixing step are as follows: about 20–60 weight percent L-zeolite; about 5–25 weight percent chromium(VI) oxide; about 10–30 weight percent binder; and about 20–40 weight percent acidic solution.

29. A process as recited in claim 18 wherein the mixture is extruded to form an extrudate which is then calcined.

30. A process as recited in claim 18 wherein the mixture is calcined at a temperature of about 400–600° C. for a time of about 1–10 hours.

* * * * *